(12) United States Patent
Gabelberger

(10) Patent No.: US 9,788,962 B2
(45) Date of Patent: Oct. 17, 2017

(54) EXPANDABLE INTERSPINOUS PROCESS SPACER IMPLANT

(71) Applicant: DePuy Synthes Products, Inc., Raynham, MA (US)

(72) Inventor: Josef Gabelberger, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/800,827

(22) Filed: Jul. 16, 2015

(65) Prior Publication Data

US 2015/0313718 A1    Nov. 5, 2015

Related U.S. Application Data

(63) Continuation of application No. 12/901,817, filed on Oct. 11, 2010.

(51) Int. Cl.
*A61B 17/70* (2006.01)
*A61F 2/44* (2006.01)

(52) U.S. Cl.
CPC ........ *A61F 2/4405* (2013.01); *A61B 17/7065* (2013.01)

(58) Field of Classification Search
CPC ......... A61B 17/7065; A61F 2002/3052; A61F 2002/30579
See application file for complete search history.

(56) References Cited

U.S. PATENT DOCUMENTS

| | | | |
|---|---|---|---|
| 6,375,683 B1 * | 4/2002 | Crozet | B65D 5/48022 623/17.15 |
| 6,699,247 B2 | 3/2004 | Zucherman et al. | |
| 7,018,415 B1 * | 3/2006 | McKay | A61F 2/4455 623/17.15 |
| 7,306,628 B2 | 12/2007 | Zucherman et al. | |
| 7,476,251 B2 | 1/2009 | Zucherman et al. | |
| 7,708,778 B2 * | 5/2010 | Gordon | A61B 17/7005 623/17.15 |
| 7,931,674 B2 | 4/2011 | Zucherman et al. | |
| 8,012,207 B2 | 9/2011 | Kim | |
| 8,109,972 B2 | 2/2012 | Zucherman et al. | |

(Continued)

FOREIGN PATENT DOCUMENTS

WO   WO 2008/044057       4/2008
WO   WO 2010/075451 A1    7/2010

*Primary Examiner* — Jan Christopher Merene
*Assistant Examiner* — Atiya Mahmud
(74) *Attorney, Agent, or Firm* — Baker & Hostetler LLP

(57) ABSTRACT

An expandable interspinous spacer implant that is configured to be inserted into an interspinous space that is defined between a spinous process of a superior vertebral body and a spinous process of an inferior vertebral body is provided. The implant may include a superior housing, an inferior housing, and a distracting member. The superior housing may have an outer surface that is configured to engage the spinous process of the superior vertebral body and the inferior housing may have an outer surface that is configured to engage the spinous process of the inferior vertebral body. The distracting member may be disposed between the superior and inferior housings, such that activation of the distracting member distracts the superior and inferior housings apart from each other.

19 Claims, 12 Drawing Sheets

(56) References Cited

U.S. PATENT DOCUMENTS

| | | |
|---|---|---|
| 8,128,702 B2 | 3/2012 | Zucherman et al. |
| 8,409,282 B2 | 4/2013 | Kim |
| 8,425,559 B2 | 4/2013 | Tebbe et al. |
| 2003/0065396 A1 | 4/2003 | Michelson |
| 2004/0153156 A1* | 8/2004 | Cohen ................ A61F 2/44 623/17.13 |
| 2006/0149229 A1 | 7/2006 | Kwak et al. |
| 2007/0032790 A1 | 2/2007 | Aschmann et al. |
| 2007/0161992 A1 | 7/2007 | Kwak et al. |
| 2007/0225706 A1 | 9/2007 | Clark et al. |
| 2007/0225807 A1 | 9/2007 | Phan et al. |
| 2007/0260245 A1 | 11/2007 | Malandain et al. |
| 2007/0270823 A1 | 11/2007 | Trieu et al. |
| 2007/0276373 A1 | 11/2007 | Malandain |
| 2008/0058937 A1 | 3/2008 | Malandain et al. |
| 2008/0071380 A1 | 3/2008 | Sweeney |
| 2008/0140207 A1 | 6/2008 | Olmos et al. |
| 2008/0177306 A1 | 7/2008 | Lamborne et al. |
| 2008/0177312 A1 | 7/2008 | Perez-Cruet et al. |
| 2008/0208344 A1 | 8/2008 | Kilpela et al. |
| 2008/0287997 A1* | 11/2008 | Altarac .............. A61B 17/7065 606/249 |
| 2009/0054988 A1 | 2/2009 | Hess |
| 2009/0222043 A1 | 9/2009 | Altarac et al. |
| 2009/0234389 A1 | 9/2009 | Chuang et al. |
| 2010/0049324 A1* | 2/2010 | Valdevit ................ A61F 2/447 623/17.16 |
| 2011/0046674 A1 | 2/2011 | Calvosa et al. |
| 2011/0066186 A1 | 3/2011 | Boyer et al. |
| 2011/0160773 A1 | 6/2011 | Aschmann et al. |
| 2011/0190816 A1 | 8/2011 | Sheffer et al. |
| 2012/0029636 A1 | 2/2012 | Ragab et al. |
| 2012/0029639 A1* | 2/2012 | Blackwell ............... A61F 2/447 623/17.16 |
| 2012/0071977 A1 | 3/2012 | Oglaza et al. |

\* cited by examiner

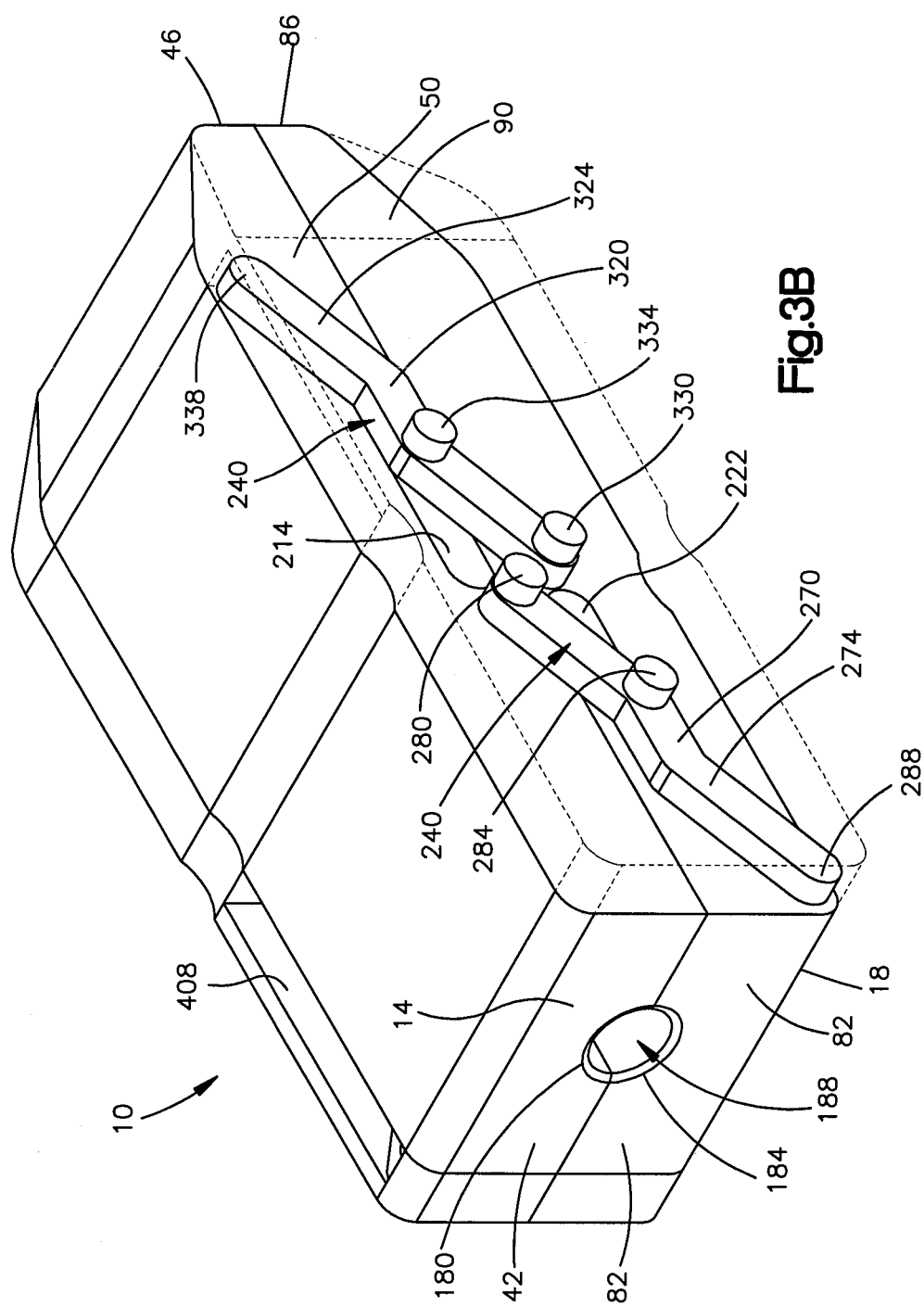

EXPANDABLE INTERSPINOUS PROCESS SPACER IMPLANT

CROSS-REFERENCE TO RELATED APPLICATIONS

This is a continuation application of U.S. patent application Ser. No. 12/901,817, filed Oct. 11, 2010, the disclosure of which is hereby incorporated by reference as if set forth in its entirety herein.

BACKGROUND

A human vertebrae has a rearward projecting portion known as a spinous process. Bending of the spine can cause the spinous processes of adjacent vertebrae to be moved toward each other. This constricts the space in the spinal canal and foramina thereby causing pain. Such constriction, which is known as stenosis, can be treated by the use of an implant in the space between adjacent spinous processes.

Some current implants are made of separate pieces which require insertion from opposite sides of the spine and in a posterior approach and necessitate rather wide openings into a patient, cutting both left and right thoracolumbar fascia as well as stripping the multifidus muscles from their attachments. It is desirable to provide an implant for insertion between the spinous processes of adjacent vertebrae which can be inserted through a single opening and may be held firmly in position between the vertebrae.

SUMMARY

An expandable interspinous spacer implant that is configured to be inserted into an interspinous space that is defined between a spinous process of a superior vertebral body and a spinous process of an inferior vertebral body is provided. The implant may include a superior housing, an inferior housing, and a distracting member. The superior housing may have an outer surface that is configured to engage the spinous process of the superior vertebral body and the inferior housing may have an outer surface that is configured to engage the spinous process of the inferior vertebral body. The distracting member may be rotatably disposed between the superior and inferior housings. The distracting member may define a first pair of opposed surfaces that define a first distance therebetween, and a second pair of opposed surfaces angularly offset with respect to the first pair of opposed surfaces. The second pair of opposed surfaces may define a second distance therebetween that is greater than the first distance.

In another embodiment the implant may include a superior housing, an inferior housing, and a deployable wing member. The superior housing may have an outer surface configured to engage the spinous process of the superior vertebral body. The inferior housing may have an outer surface configured to engage the spinous process of the inferior vertebral body. The deployable wing member may be rotatably coupled to the superior housing and translatably guided through a slot defined by the inferior housing.

In another embodiment the implant may include a superior housing, an inferior housing, a distracting member, and at least one deployable wing member. The superior housing may have an outer surface configured to engage the spinous process of the superior vertebral body. The inferior housing may have an outer surface configured to engage the spinous process of the inferior vertebral body. The distracting member may be disposed between the superior and inferior housings. Movement of the distracting member from a first position to a second position distracts the superior and inferior housings apart from each other. The at least one wing member includes an extension, and is rotatably coupled to a respective one of the superior and inferior housings, such that movement of the distraction member from the first position to the second position causes the at least one wing member to rotate about the respective housing to thereby cause the extension to extend out a respective housing.

BRIEF DESCRIPTION OF THE DRAWINGS

The foregoing summary, as well as the following detailed description of illustrative embodiments of the instrument of the present application, will be better understood when read in conjunction with the appended drawings. For the purposes of illustrating the interspinous spacer implant of the present application, there is shown in the drawings illustrative embodiments. It should be understood, however, that the application is not limited to the precise arrangements and instrumentalities shown. In the drawings:

FIG. 3B is a perspective view of the expandable interspinous process spacer implant of FIG. 2, with a superior second lateral side cover plate and an inferior second lateral side cover plate removed;

DETAILED DESCRIPTION OF ILLUSTRATIVE EMBODIMENTS

Figure 1:
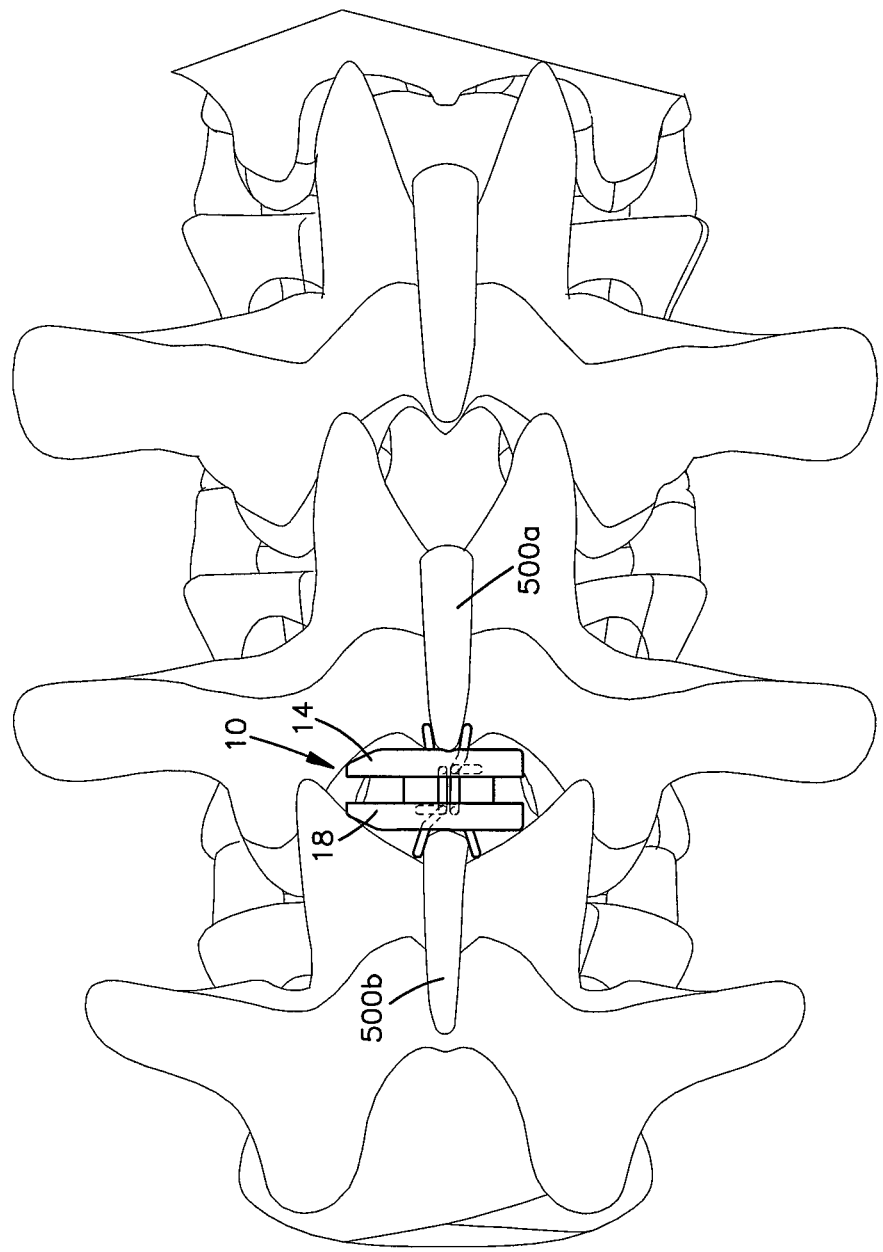
FIG. 1 is a perspective view of an expandable interspinous process spacer implant in accordance with one embodiment after it has been inserted into a space defined between adjacent spinous processes.

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the patient's body, or the geometric center of the interspinous spacer implant and related parts thereof. The words, "anterior", "posterior", "superior," "inferior" and related words and/or phrases designate preferred positions and orientations in the human body to which reference is made and are not meant to be limiting. The terminology includes the above-listed words, derivatives thereof and words of similar import.

Figure 2:
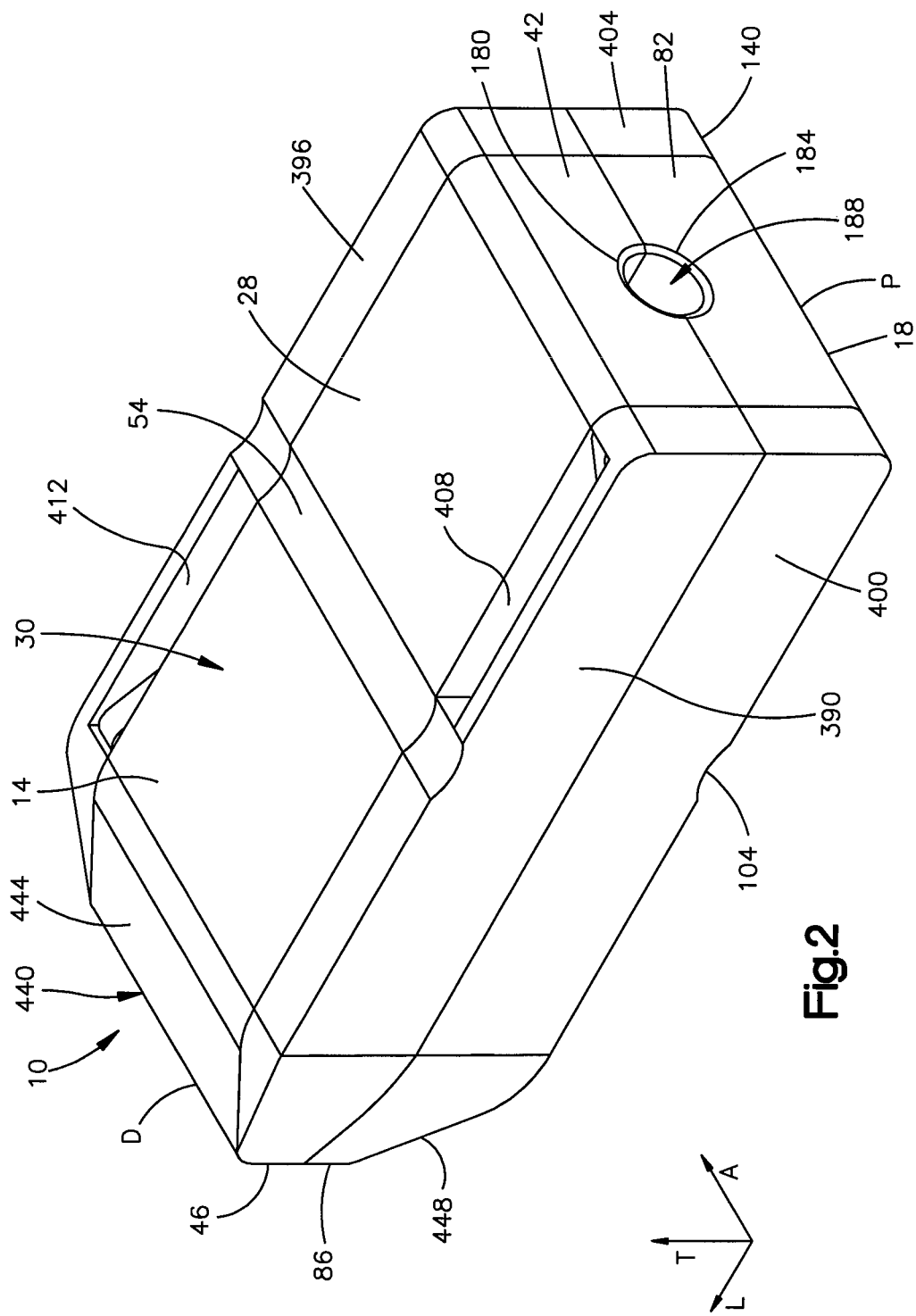
FIG. 2 is a perspective view of the expandable interspinous process spacer implant shown in FIG. 1, in a collapsed configuration.

In reference to FIGS. 1 and 2, an expandable interspinous process spacer implant 10 that is configured to be inserted into a space defined between a spinous process 500*a* of a superior vertebral body and a spinous process 500*b* of an inferior vertebral body is provided. The implant 10 is described herein as extending horizontally along a longitudinal direction "L" and lateral direction "A", and vertically along a transverse direction "T". Unless otherwise specified herein, the terms "lateral," "longitudinal," and "transverse" are used to describe the orthogonal directional components of various components. It should be appreciated that while the longitudinal and lateral directions are illustrated as extending along a horizontal plane, and that the transverse direction is illustrated as extending along a vertical plane, the planes that encompass the various directions may differ during use. For instance, when the spacer implant 10 is implanted into a space defined between adjacent spinous processes such as spinous processes 500*a* and 500*b*, the transverse direction T extends generally along the superior-inferior (or caudal-cranial) direction, while the plane defined by the longitudinal direction L and lateral direction A lie generally in the anatomical plane defined by the anterior-posterior direction, and the medial-lateral direction. Accordingly, the directional terms "vertical" and "horizontal" are used to describe the spacer implant 10 and its components as illustrated merely for the purposes of clarity and illustration.

As shown in FIG. 1, the implant 10 is configured to be inserted into a space defined between adjacent spinous processes such as spinous processes 500*a* and 500*b*. The implant 10 extends along a longitudinal direction L from a proximal end P to a distal end D. In the embodiment illustrated, the longitudinal direction L may also be considered the insertion direction. As shown in FIG. 2, the implant 10 includes a superior housing 14, an inferior housing 18, and a distracting member 22 disposed between the superior and inferior housings 14, 18. By activating (i.e. translating, rotating, etc.) or otherwise moving the distracting member 22 from a first position to a second position, the superior and inferior housing 14, 18 will be distracted apart from one another and the implant will be converted from a first or insertion or collapsed configuration to a second or expanded configuration. In the illustrated embodiment, the distracting member 22 is an oblong cam member 24 that is configured to be rotated, such that upon a 90 degree rotation, the superior and inferior housings 14, 18 are distracted apart from one another to thereby distract the adjacent spinous process apart from one another.

As shown in FIGS. 2-6, the superior housing 14 includes a body 28 that defines an upper, or superior, or outer, engagement surface 30 that is configured to contact the spinous process of the superior vertebral body, and a lower, or inferior, surface 34 that defines a void 38 configured to at least partially house the cam member 24. The body 28 further defines a proximal side 42, a distal side 46, and opposing lateral sides 50 that join the proximal side 42 and distal side 46.

As shown in FIG. 2, the upper surface 30 of the superior housing 14 defines a notch 54 that extends transversely across a middle portion of the upper surface 30. The notch 54 is configured to engage and receive the spinous process of the superior vertebral body when the implant 10 is in an expanded configuration. Such a configuration helps align and secure the implant 10 within the space between the adjacent spinous processes.

Figure 4:
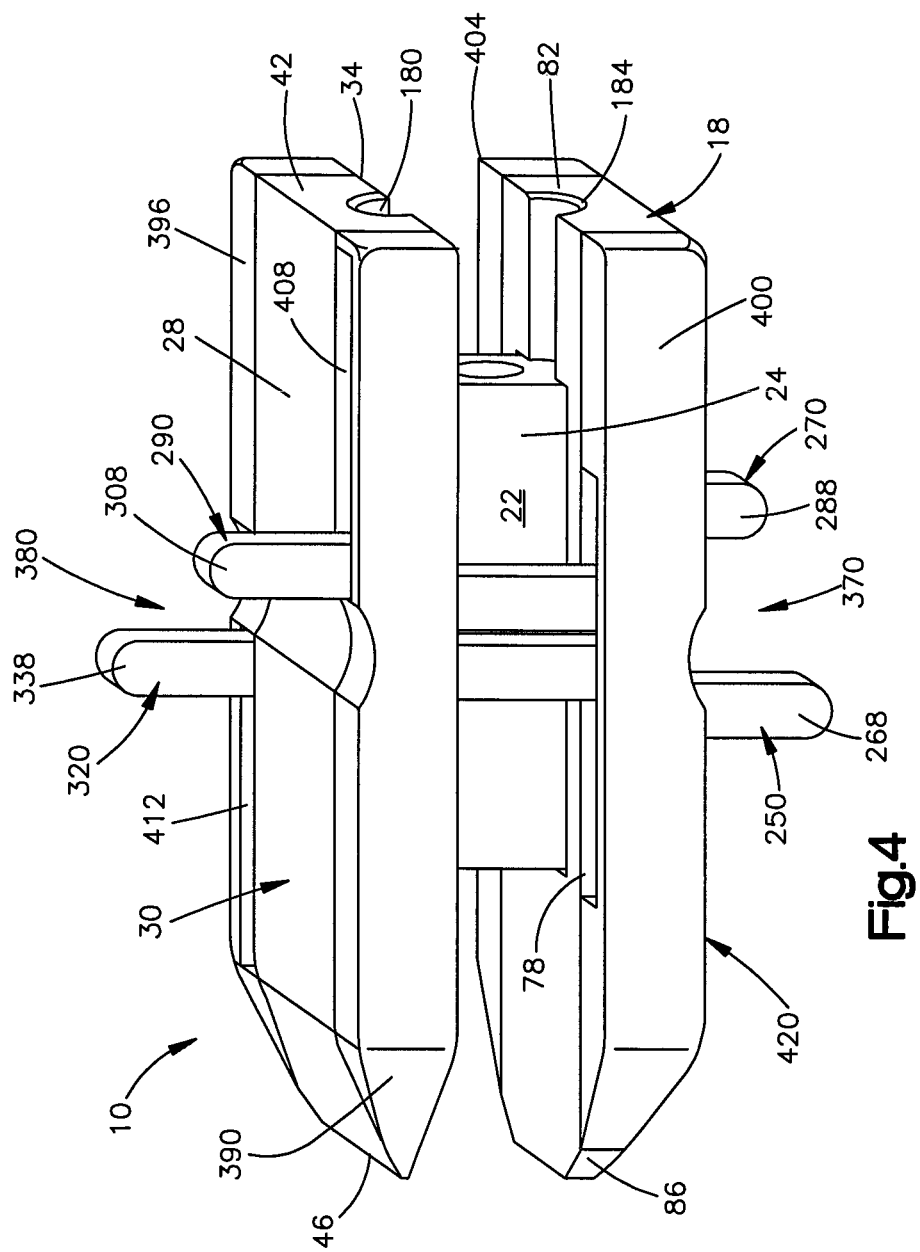
FIG. 4 is a perspective view of the expandable interspinous process spacer implant of FIG. 2 in an expanded configuration.
Figure 5:
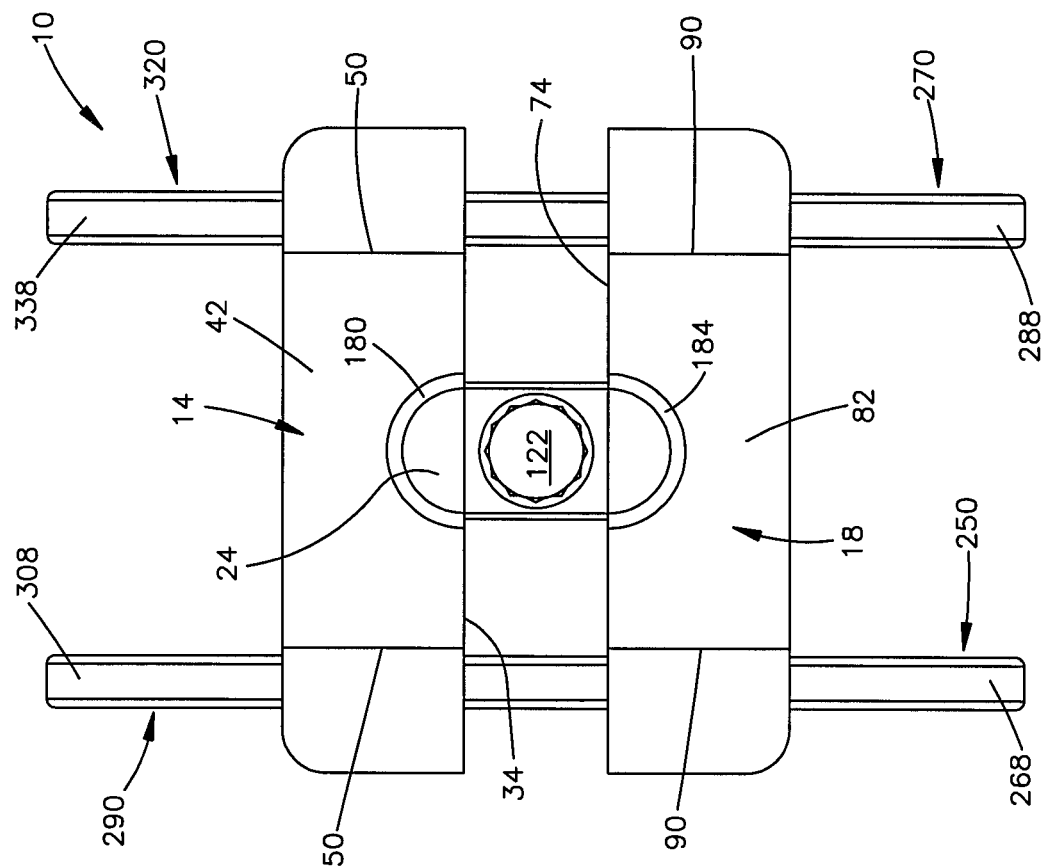
FIG. 5 is a rear end elevational view of the expandable interspinous process spacer implant of FIG. 2 in an expanded configuration.
Figure 6:
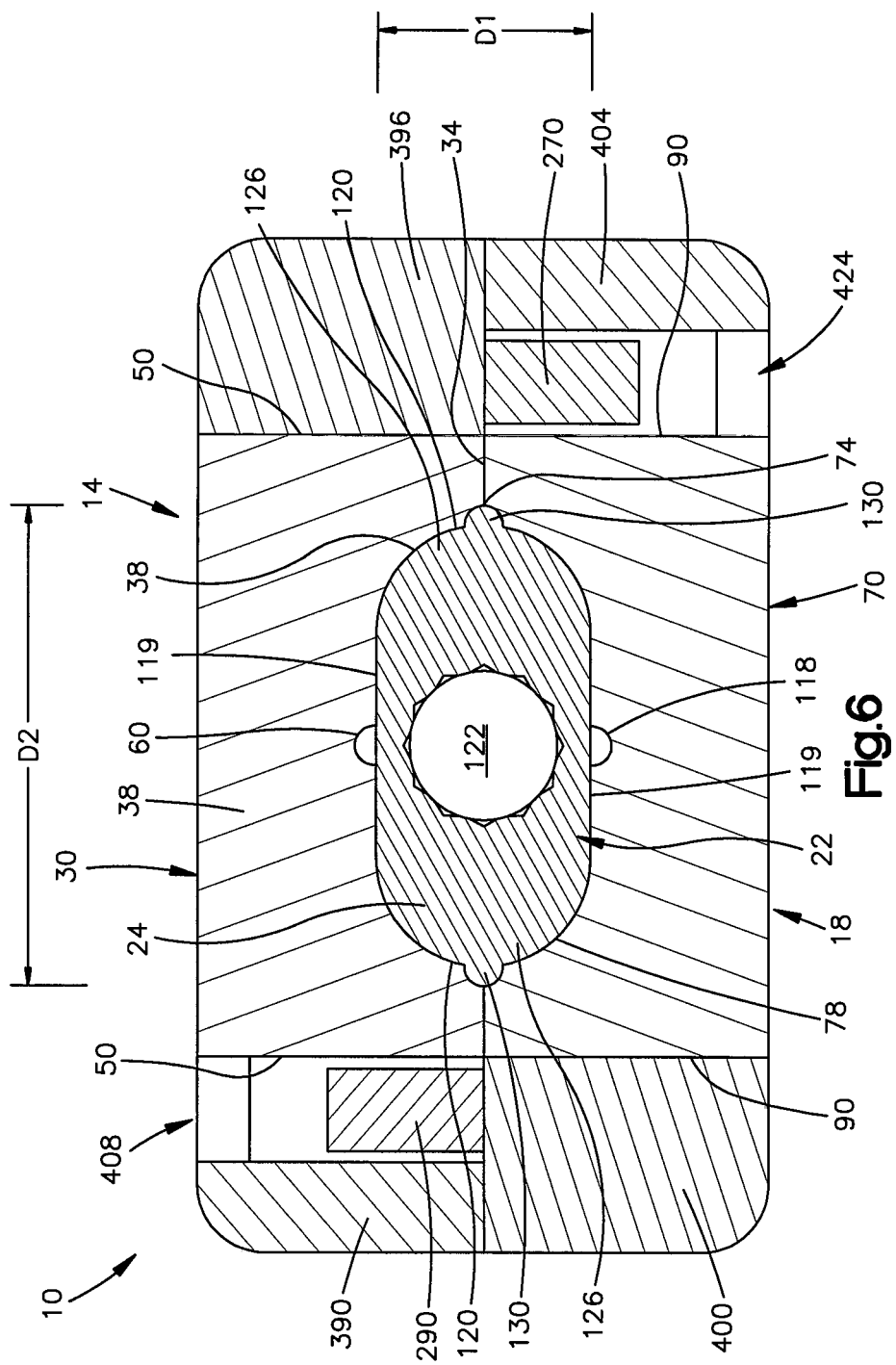
FIG. 6 is a rear cross sectional view of the expandable interspinous process spacer implant of FIG. 2 in a collapsed configuration.

As best shown in FIGS. 4 and 6, the void 38 extends vertically into the inferior surface 34 of the superior housing 14 and along the inferior surface 34 in the longitudinal direction L. As best shown in FIG. 5, the void 38 is oblong in the lateral direction A and is configured to house the oblong cam member 24. Furthermore, the void 38 defines a recess 60 that is configured to be engaged by a protrusion extending from the cam member 24 when the cam member 24 has been moved from the first position to the second position.

Similarly, the inferior housing 18 includes a body 68 that defines a lower, or inferior, or outer, engagement surface 70 that is configured to contact the spinous process of the inferior vertebral body, and an upper, or superior, surface 74 that defines a void 78 configured to at least partially house the cam member 24. The body 68 further defines a proximal side 82, a distal side 86, and opposing lateral sides 90 that join the proximal side 82 and distal side 86.

As shown in FIG. 2, the lower surface 70 of the inferior housing 18 defines a notch 104 that extends transversely across a middle portion of the lower surface 70. The notch 104 is configured to engage and receive the spinous process of the inferior vertebral body when the implant 10 is in the expanded configuration. Such a configuration helps align and secure the implant 10 within the space between the adjacent spinous processes.

As shown in FIGS. 4-6, the void 78 extends vertically into the superior surface 74 of the inferior housing 18 and along the inferior surface 34 in the longitudinal direction L. As best shown in FIG. 4, the void 78 is oblong in the lateral direction A and is configured to house the oblong cam member 24. In particular, the void 38 defined in the superior housing 14 and the void 78 defined in the inferior housing 18, together define a cavity 114 that encapsulates the oblong cam member 24. Furthermore, the void 78 defines a recess 118 that is configured to be engaged by a protrusion extending from the cam member 24 when the cam member 24 has been moved from the first position to the second position. As shown in FIG. 6, the recess 118 of the void 78 opposes the recess 60 of the void 38.

As shown in FIGS. 4-6, the cam member 24 is encapsulated within the cavity 114 defined by the voids 38, 78 of the superior and inferior housings 14, 18, and is configured to distract the superior and inferior housings 14, 18 away from each other when moved from the first position to the second position. The cam member 24 defines a first pair of opposed surfaces 119 that define a first distance D1 therebetween and a second pair of opposed surfaces 120 that defined a second distance D2 therebetween. The second pair of opposed surfaces 120 are angularly offset with respect to the first pair of opposed surfaces 119 by 90 degrees, and the second distance D2 is greater than the first distance D1.

As shown in FIG. 6, the cam member 24 is oblong in the lateral direction when in the first position. That is, the first opposed surfaces 119 of the cam member 24 engage the housings 14, 18, when the superior and inferior housings 14, 18 have not been distracted apart from each other. When the cam member 24 has been rotated to the second position the cam member is oblong in the transverse direction and the opposed second surfaces 120 engage the housings 14, 18 to thereby cause the housings 14, 18 to distract from each other.

Also shown in FIG. 6, the second opposed surfaces 120 define curved lateral ends 126. Extending laterally outward from each lateral end 126 is a protrusion 130 that is configured to engage a respective recess 78, 118 defined in the voids 38, 78 of the superior and inferior housings 14, 18. During insertion of the implant 10, the cam member 24 is oblong in the lateral direction as shown in FIG. 6, and the protrusions 130 extend laterally outward. When the cam member 24 is rotated 90 degrees, as shown in FIG. 5, the protrusions 130 extend transversely outward and will engage the respective recesses 78, 118 defined in the housing voids 38, 78 to thereby lock the implant 10 in the expanded configuration. It should be understood that the protrusions 130 may extend out from the cam member 24 anywhere along its length. For example, the protrusions 130 may be angularly offset from each other by 90 degrees.

As shown in FIG. 6, a proximal end of the cam member 24 defines an instrument engagement feature 122 that extends longitudinally into the cam member 24. The instrument engagement feature 122 may define a star that is configured to receive a star drive, such that rotation of the star drive rotates the cam member 24 to thereby move the cam member 24 from the first position to the second position.

As best shown in FIGS. 2 and 4, the superior and inferior housings 14, 18 provide access to the instrument engagement feature 122 of the cam member 24 when the implant 10 is in the collapsed configurations. In that regard, the superior housing 14 further defines a superior semi-cylindrical groove 180 that extends into the proximal side 42 of the superior housing 14 and into the void 38 of the superior housing 14, while the inferior housing 18 further defines an inferior semi-cylindrical groove 184 that extends into the proximal side 82 of the inferior housing and into the void 78 of the inferior housing 18. As shown in FIG. 2, the superior semi-cylindrical groove 180 and the inferior semi-cylindrical groove 184 combine to form an access bore 188 when the implant 10 is in a collapsed configuration. The access bore 188 is configured to provide access for the driver instrument so that the instrument can engage the instrument engagement feature 122 of the cam member 24 to thereby insert the implant 10 and activate or otherwise move the cam member 24 once the implant is properly positioned.

Figure 3A:
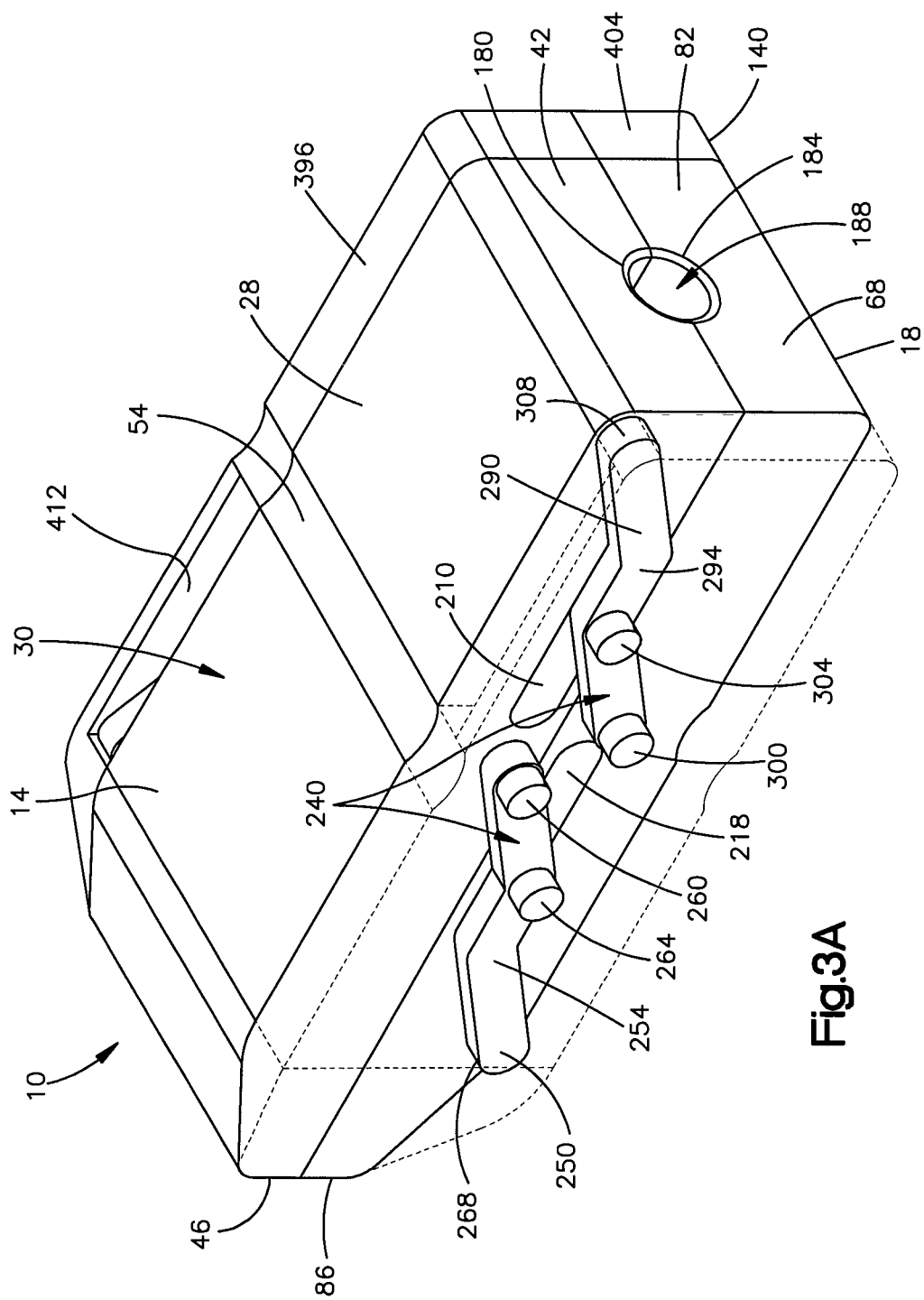
FIG. 3A is a perspective view of the expandable interspinous process spacer implant of FIG. 2, with a superior first lateral side cover plate and an inferior first lateral side cover plate removed.

As best shown in FIGS. 3A and 3B, the superior and inferior housings 14, 18 further define oblong slots that are defined in their lateral sides. As shown, the superior housing 14 includes a first superior oblong slot 210 that extends in the longitudinal direction L along a first lateral side 50 of the superior housing 14 and a second superior oblong slot 214 that extends in the longitudinal direction L along a second lateral side 50 of the superior housing 14. The first slot 210 extends distally along the first lateral side 50 from a point that is proximate to the proximal end 42 of the housing 14 to a point that is proximate to a midline of the housing 14. The second slot 214 extends distally along the second lateral side 50 from a point that is proximate to the midline of the housing 14 to a point that is proximate to the distal end 46 of the housing 14. The slots 210 and 214 are configured to act as guidance tracks for their respective wing members.

Similarly, the inferior housing 18 includes a first inferior oblong slot 218 that extends in the longitudinal direction L along a first lateral side 90 of the inferior housing 18 and a second inferior oblong slot 222 that extends in the longitudinal direction L along a second lateral side 90 of the inferior housing 18. The first slot 218 extends distally along the first lateral side 90 from a point that is proximate to a midline of the housing 18 to a point that is proximate to the distal end 86 of the housing 18. The second slot 222 extends distally along the second lateral side 90 from a point that is proximate to the proximal end 82 of the housing 18 to a point that is proximate to the midline of the housing 18. The slots 218 and 222 are configured to act as guidance tracks for their respective wing members.

As shown in FIGS. 3A and 3B, the implant 10 further includes a stabilizer 240 that comprises a plurality of deployable wing members that are rotatably coupled to one of the superior and inferior housings 14, 18, and translatably coupled to the other of the superior and inferior housings 14, 18. The stabilizer is configured to engage respective spinous processes of the superior and inferior vertebral bodies when the implant 10 is in an expanded configuration. As shown in FIGS. 3A and 3B, the implant 10 includes a first wing member 250 having a body 254 that defines a superior end that is rotatably coupled to the superior housing 14 proximate to a distal end of the superior housing's first slot 210. The first wing member 250 is rotatably coupled to the superior housing 14 with a first securement pin 260. A middle portion of the first wing member 250 is translatably coupled to the first slot 218 of the inferior housing 18 with a first guidance pin 264. When the superior and inferior housings 14, 18 are distracted apart, the first wing member 250 rotates counterclockwise about the securement pin 260 and translates proximally or is otherwise guided within the first slot 218. Once fully distracted, a first extension portion 268 of the first wing member 250 protrudes from or otherwise extends below the inferior surface of the inferior housing 18.

The implant 10 further includes a second wing member 270 having a body 274 that defines a superior end that is rotatably coupled to the superior housing 14 proximate to a proximal end of the superior housing's second slot 214. The second wing member 270 is rotatably coupled to the superior housing 14 with a second securement pin 280. A middle portion of the second wing member 270 is translatably coupled to the second slot 222 of the inferior housing 18 with a second guidance pin 284. When the superior and inferior housings 14, 18 are distracted apart, the second wing member 270 rotates clockwise about the securement pin 280 and translates distally or is otherwise guided within the second slot 222. Once fully distracted a second extension portion 288 of the second wing member 270 protrudes from or otherwise extends below the inferior surface of the inferior housing 18.

The implant 10 further includes a third wing member 290 having a body 294 that defines an inferior end that is rotatably coupled to the inferior housing 18 proximate to a proximal end of the inferior housing's first slot 218. The third wing member 290 is rotatably coupled to the inferior housing 18 with a third securement pin 300. A middle portion of the third wing member 290 is translatably coupled to the first slot 210 of the superior housing 14 with a third guidance pin 304. When the superior and inferior housings 14, 18 are distracted apart, the third wing member 290 rotates counterclockwise about the securement pin 300 and translates distally or is otherwise guided within the first slot 210. Once fully distracted a third extension portion 308 of the third wing member 290 protrudes from or otherwise extends above the superior surface of the superior housing 14.

The implant 10 further includes a fourth wing member 320 having a body 324 that defines an inferior end that is rotatably coupled to the inferior housing 18 proximate to a distal end of the inferior housing's second slot 222. The fourth wing member 320 is rotatably coupled to the inferior housing 18 with a fourth securement pin 330. A middle portion of the fourth wing member 320 is translatably coupled to the second slot 214 of the superior housing 14 with a fourth guidance pin 334. When the superior and inferior housings 14, 18 are distracted apart, the fourth wing member 320 rotates clockwise about the securement pin 330 and translates proximally or is otherwise guided within the second slot 214. Once fully distracted a fourth extension portion 338 of the fourth wing member 320 protrudes from or otherwise extends above the superior surface of the superior housing 14.

As shown in FIG. 4, when the implant 10 is in an expanded configuration the first extension 268 of the first wing member 250 and the second extension 288 of the second wing member 270 protrude from and extend below the inferior surface of the inferior housing 18. As shown, the first and second extensions 268, 288 define a gap 370 that is configured to receive the spinous process of the inferior vertebral body. In this way, the first and second wing members 250, 270 engage the spinous process to thereby hold the implant 10 firmly in place.

Similarly, when the implant 10 is in an expanded configuration the third extension 308 of the third wing member 290 and the fourth extension 338 of the fourth wing member 320 protrude from and extend above the superior surface of the superior housing 14. As shown, the third and fourth extensions 308, 338 define a gap 380 that is configured to receive the spinous process of the superior vertebral body. In this way, the third and fourth wing members 290, 320 engage the spinous process to thereby hold the implant 10 firmly in place.

As shown in FIGS. 2-6, the implant 10 further includes cover plates to cover the wing members. As shown, the implant 10 includes a superior first lateral side surface cover plate 390 and a superior second lateral side surface cover plate 396 that are each configured to couple to the first and second lateral sides, respectively, of the superior housing 14. Similarly, the implant 10 includes an inferior first lateral side surface cover plate 400 and an inferior second lateral side surface cover plate 404 that are configured to couple to the first and second lateral sides, respectively, of the inferior housing 18. The cover plates 390, 396, 400, and 404 may shield the wing members from any debris that may prevent them from functioning.

When the cover plates 390, 396, 400, and 404 are attached to the lateral sides of their respective housing bodies, openings are provided for the wing members to extend through when the implant is in an expanded configuration. As shown in FIG. 4, a first superior opening 408 is provided between the first lateral side of the superior housing body 28 and the superior first lateral side cover plate 390, and a second superior opening 412 is provided between the second lateral side of the superior housing body 28 and the superior second lateral side cover plate 396. The openings 408 and 412 are configured to allow the superior ends of the third wing member 290 and the fourth wing member 320 to deploy therethrough upon expansion of the implant 10.

Similarly, a first inferior opening 420 is provided between the first lateral side of the inferior housing body 68 and the inferior first lateral side cover plate 400, and a second inferior opening 424 is provided between the second lateral side of the inferior housing body 68 and the inferior second lateral side cover plate 404. The openings 420 and 424 are configured to allow the inferior ends of the first wing member 250 and the second wing member 270 to deploy therethrough upon expansion of the implant 10.

Referring back to FIG. 2, the distal sides 46, 86 of the superior housing 14 and the inferior housing 18 are tapered such that the implant 10 is provided with a bullet-nosed tip 440 when the implant is in a collapsed configuration. In particular, the distal side 46 of the superior housing 14 includes a distraction surface 444 that angles transversely out as it extends proximally. Similarly, the distal side 86 of the inferior housing 18 includes a distraction surface 448 that angles transversely out as it extends proximally. Such a design helps to ease the insertion of the implant 10 into the interspinous space as well as to provide an initial amount of distraction to the adjacent spinous processes.

Figure 7A:
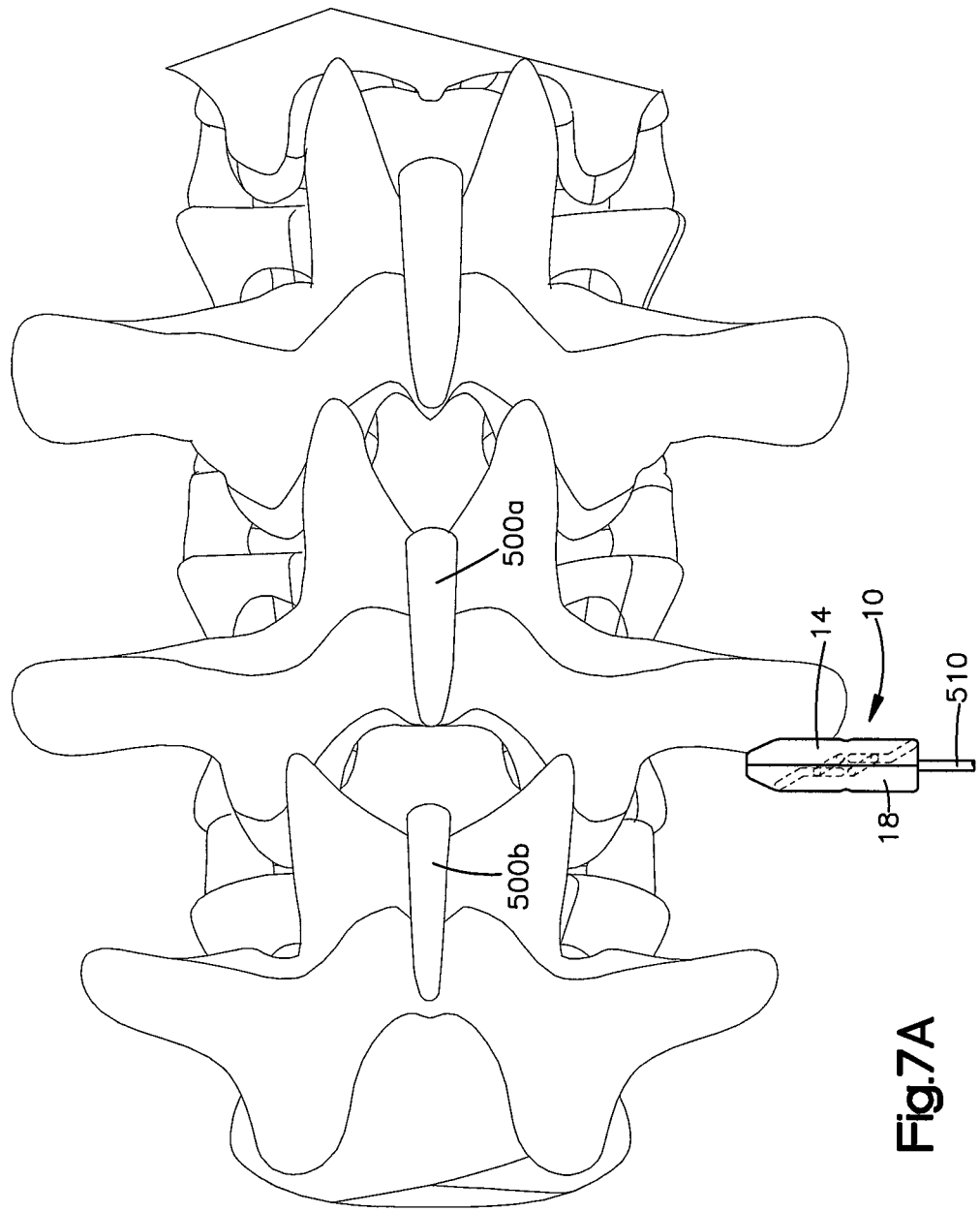
FIG. 7A is a perspective view of the expandable interspinous process spacer implant of FIG. 2 being inserted into a space defined between adjacent spinous processes.

In operation, and in reference to FIGS. 7A-7E, adjacent spinous processes 500a and 500b between which the treatment of spinal stenosis is desired are identified and an incision is made in the back of the patient. In one embodiment, the incision is made to accommodate a lateral approach, although it should be understood that a variety of approach angles are appropriate for use with the present implant. As shown in FIG. 7A, the distal end of an instrument 510 is inserted into the access opening 188 defined by the collapsed implant housings 14, 18 and is mated with or otherwise engages the instrument engagement feature 122 defined by the cam member 24, to thereby couple the implant 10 to the instrument 510. While in a collapsed configuration, the wing members are for the most part are not protruding from the housings 14, 18, and the implant 10 is inserted into the space defined between the adjacent spinous processes 500a, 500b using the instrument 510. The bullet-nosed distal tip of the implant 10 eases the insertion and may provide an amount of distraction to the spinous processes 500a, 500b during insertion.

Once the surgeon determines that the implant 10 is disposed at a desired position between the adjacent spinous processes 500a, 500b, and the inferior surface of the superior spinous process 500a is disposed within the notch 54 defined in the superior housing 14, and the superior surface of the inferior spinous process 500b is disposed within the notch 104 defined by the inferior housing 18, e.g., using fluoroscopy or a CT scan, the instrument 510 is rotated 90 degrees, which thereby rotates the cam member 24 from the first position to the second position and distracts the superior housing 14 away from the inferior housing 18. Once the cam member 24 has been moved to the second position, or otherwise turned 90 degrees, the first and second cam protrusions 130 engage the first and second recesses 78, 118 of the superior and inferior housing voids, respectively to lock the implant 10 in its expanded configuration.

Figure 7B:
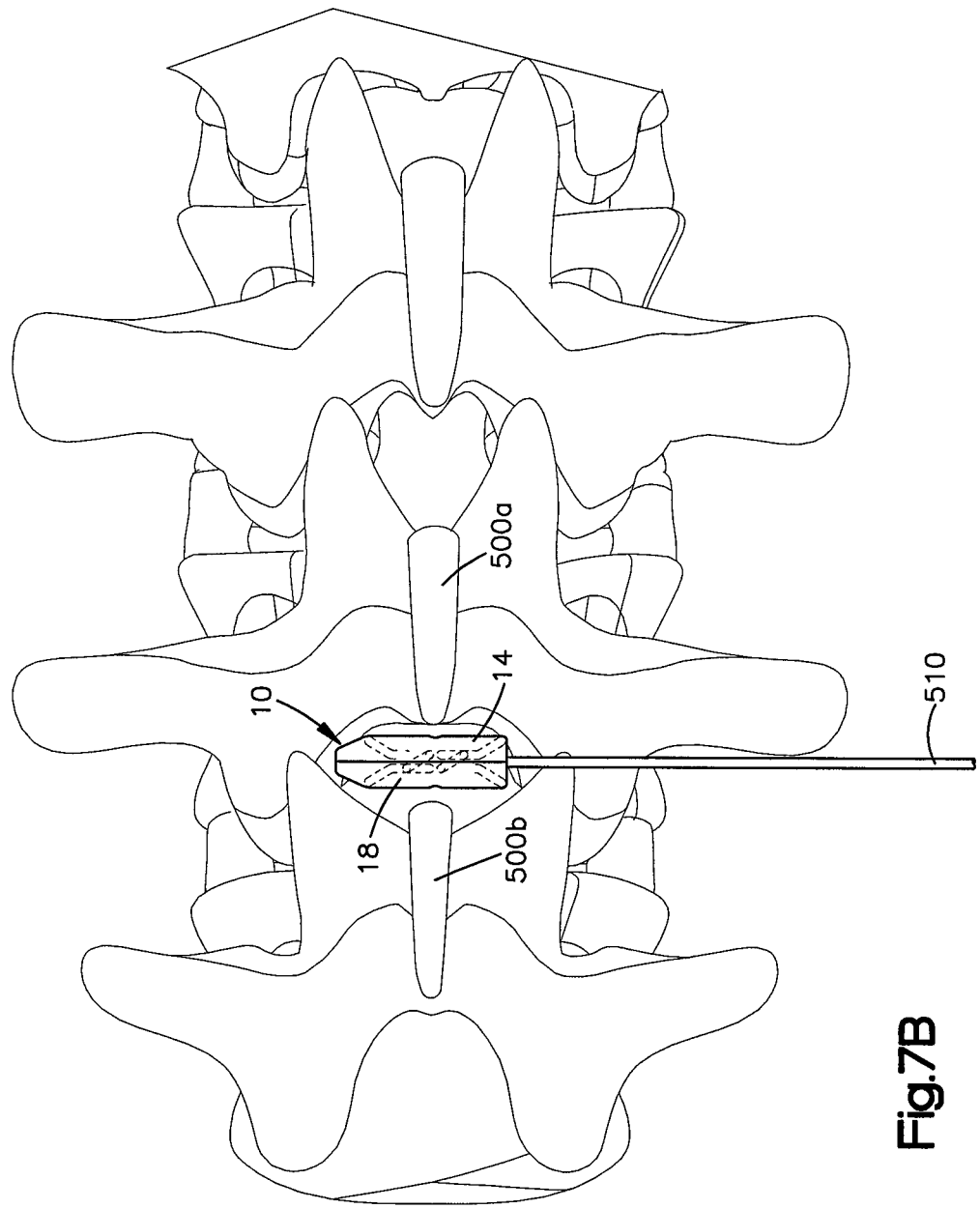
FIG. 7B is a perspective view of the expandable interspinous process spacer implant of FIG. 7A, after the spacer has been fully inserted into the space defined between the adjacent spinous processes.
Figure 7C:
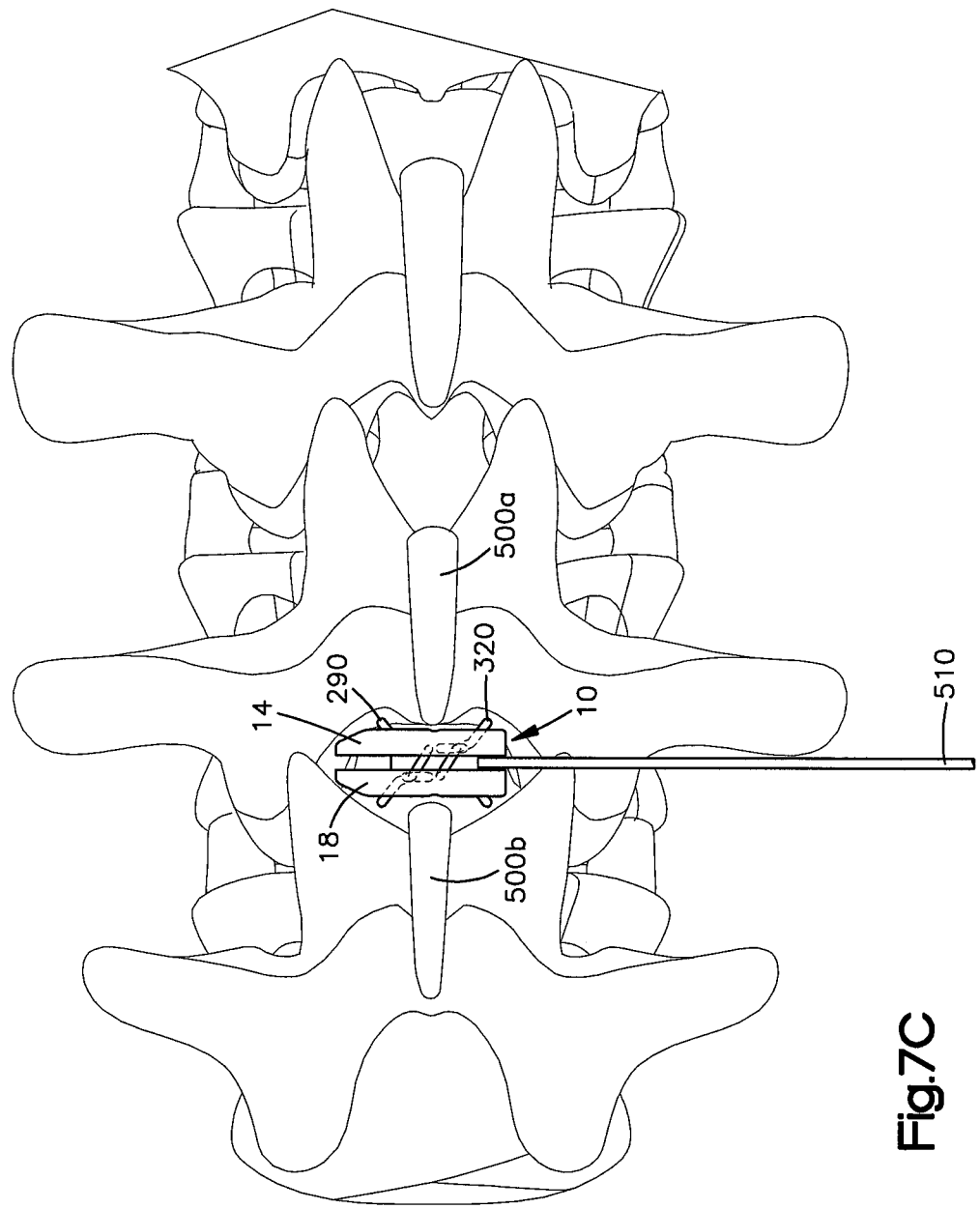
FIG. 7C is a perspective view of the expandable interspinous process spacer implant of FIG. 7B in a partial expanded position.
Figure 7D:
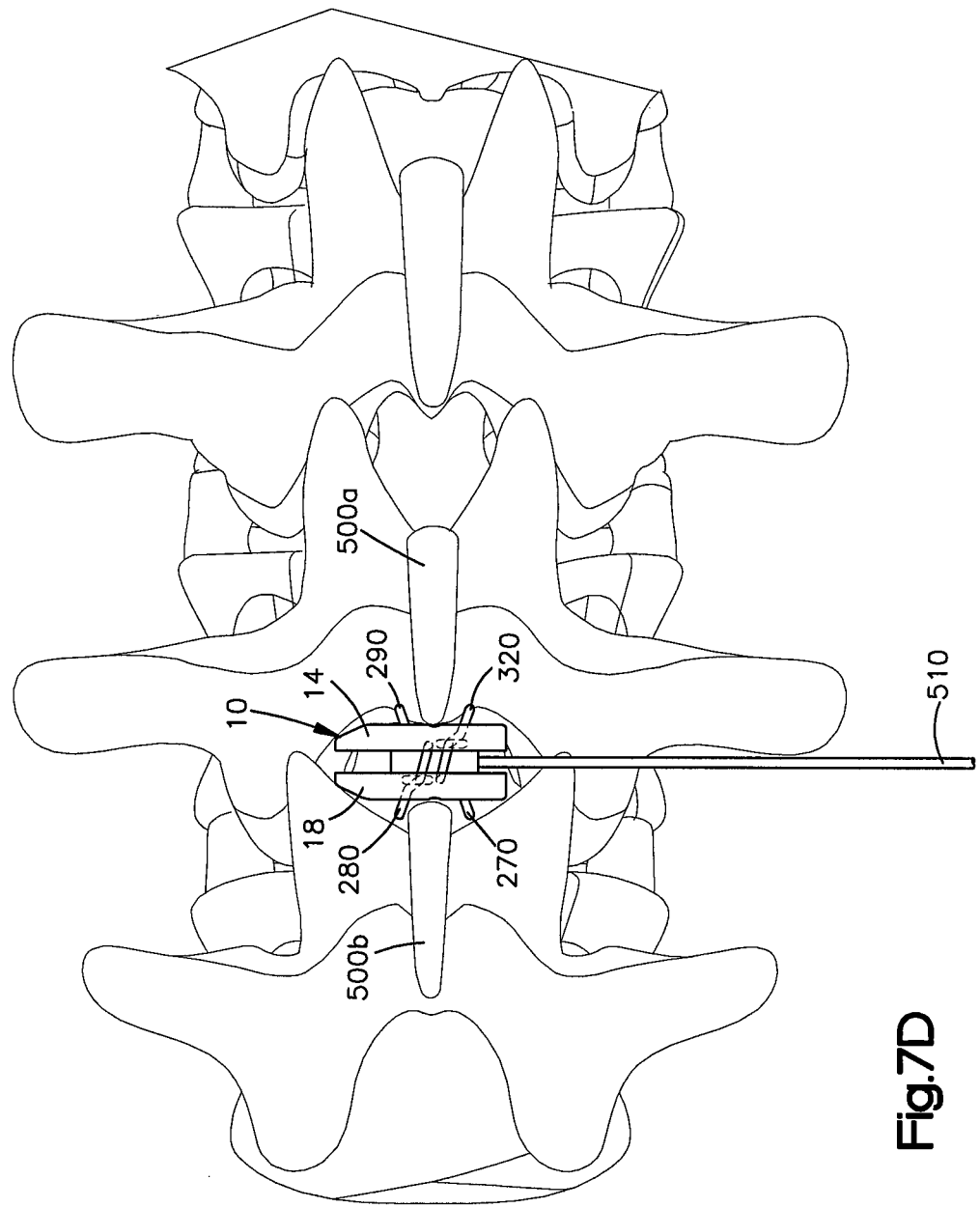
FIG. 7D is a perspective view of the expandable interspinous process spacer implant of FIG. 7C in a partial expanded position.
Figure 7E:
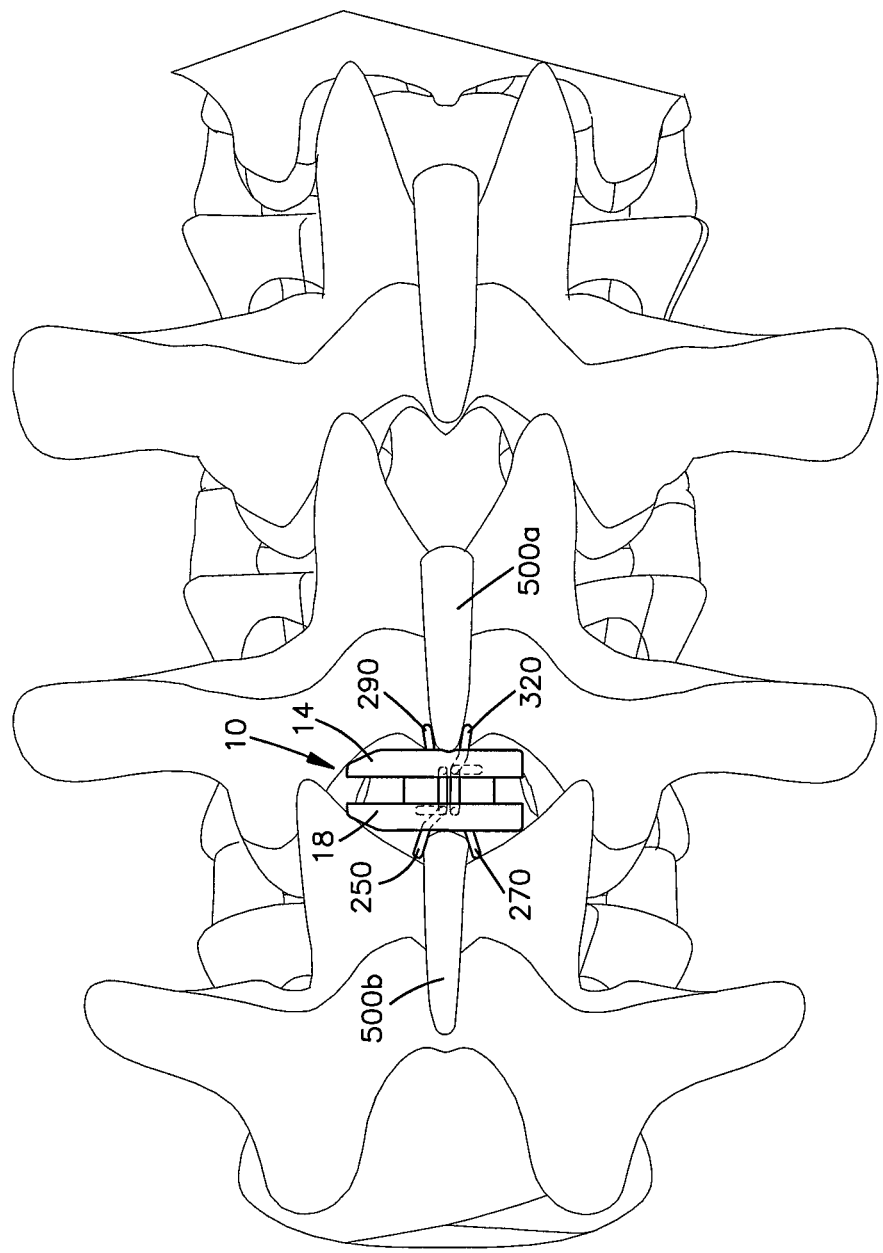
FIG. 7E is a perspective view of the expandable interspinous process spacer implant of FIG. 7D in a fully expanded position.

As shown in FIGS. 7B-7D, during the expansion of the implant 10 caused by the rotation of the cam member 24 by the instrument 510, the first wing 250, the second wing 270, the third wing 290, and the fourth wing 320 automatically deploy through the first inferior opening 420, the first superior opening 408, the second inferior opening 424, and the second superior opening 412, respectively. That is, the first wing 250, the second wing 270, the third wing 290, and the fourth wing 320 articulate about their respective securement pins 260, 280, 300, and 330, as they translate within their respective guidance tracks or slots 218, 222, 210, and 214 to thereby protrude outward from the housings 14 and 18 as shown in FIG. 7D. Once the implant 10 assumes its expanded configuration, the first, second, third, and fourth wings 250, 270, 290, and 320 secure the implant 10 with respect to the adjacent spinous processes 500a, 500b and the instrument 510 is disengaged from the cam member 24 and removed as shown in FIG. 7E.

The components of the implant 10 are formed from implant-grade plastics such as PEEK or ultra high molecular weight polyethylene (UHMWPE); however, a variety of biocompatible materials such as titanium and its alloys, stainless steel, cobalt-chromium, biocompatible polymers, and bone material such as allograft can be utilized to form one or more of the components of the implant 10. Further, a combination of materials can be envisioned as suitable for forming the implant 10, such as the inclusion of PEEK to form the superior and inferior housings 14, 18 and the inclusion of titanium to form the distraction member 22 and the wings 250, 270, 290, and 320. Further, depending upon the choice of materials used to form the implant 10 and its various components, the implant 10 may provide expansion on a continuum from soft and flexible to completely rigid. There may further be a dampening or cushioning component disposed within the implant 10 that provides a desired amount of flexibility with a stop element to prevent deflection of the implant 10 beyond a predetermined limit.

It should be understood that the distraction member may include a variety of designs that could expand the implant to its expanded configuration. For example, in an alternate embodiment, the distracting member 22 can be replaced with a wedge member that can be pulled or pushed into matching wedge-shaped recesses defined on the inferior surface of the superior housing 14 and/or the superior surface of the inferior housing 18 to thereby expand the implant 10. In yet another alternate embodiment, the distracting member 22 can be replaced with a turnbuckle that, upon rotation about a vertical axis, distracts the superior and inferior housings 14, 18. In yet another alternate embodiment, the distracting member 22 can be replaced with a plurality of camming elements that rotate in the same or opposite directions. Such a plurality of camming elements may include features that couple the camming elements' motion in order to add stability to the implant in its expanded configuration. In yet another alternate embodiment, the distracting member 22 can be replaced with a member featuring conical male threads mating with conical female threads on the insides of the superior housing 14 and the inferior housing 18.

It should also be understood that the implant 10 may include any number of wings and is not limited to four wings as shown in the illustrated embodiment. For example, the implant 10 may have additional wings that may be disposed, for example, at the center of the implant 10. In yet another embodiment, only two wings may be included in the design. Further the wings do not have to rotate as shown. For example, the implant 10 may include a pair of fixed wings on a first side of the implant 10 and a pair of deployable wings on a second side of the implant 10.

It will be appreciated by those skilled in the art that changes could be made to the embodiments described above without departing from the broad inventive concept thereof. Furthermore, it should be appreciated that the structure, features, and methods as described above with respect to any of the embodiments described herein can be incorporated into any of the other embodiments described herein unless otherwise indicated. It is understood, therefore, that this invention is not limited to the particular embodiments disclosed, but it is intended to cover modifications within the spirit and scope of the present disclosure.

What is claimed:

1. An expandable spacer implant configured to be inserted into a space that is defined between a superior vertebral body and an inferior vertebral body that are spaced from one another along a first direction, the implant comprising:
   a proximal-most side of the implant, a distal-most side of the implant spaced from the proximal-most side along a second direction, perpendicular to the first direction, and a middle portion of the implant that is midway between the proximal-most side and the distal-most side;
   a first housing having an outer surface configured to engage one of the superior and inferior vertebral bodies, and an inner surface spaced from the outer surface along the first direction;
   a second housing that extends between the proximal-most side and the distal-most side at the middle portion of the implant, the second housing having an inner surface that faces the inner surface of the first housing, and an outer surface spaced from the outer surface of the first housing along the first direction, the outer surface of the second housing configured to engage another of the superior and inferior vertebral bodies, the second housing including a first pair of internal surfaces that face one another, and a second pair of internal surfaces that face one another, the first and second pairs of internal surfaces at least partially defining a void that extends into the inner surface of the second housing, the first pair of internal surfaces spaced along the second direction and the second pair of internal surfaces spaced along a third direction, perpendicular to both the first and second directions; and
   a distracting member disposed within the void between the first and second housings, and rotatable about an axis of rotation that extends along the second direction, the distracting member defining a first pair of opposed surfaces that define a first distance therebetween, and a second pair of opposed surfaces angularly offset with respect to the first pair of opposed surfaces about the axis of rotation, the second pair of opposed surfaces defining a second distance therebetween that is greater than the first distance, wherein the first and second housings each have an overall length along the second direction that is greater than an overall length of the distracting member along the second direction, and the implant is expandable by rotating the distracting member about the axis of rotation such that the second pair of opposed surfaces engage the first and second housings to cause the first and second housings to move away from one another along the first direction.

2. The expandable spacer implant of claim 1, wherein each of the first and second housings defines a void that extends into a respective one of the inner surfaces of the first and second housings.

3. The expandable spacer implant of claim 2, wherein each of the first and second housings includes first and second pairs of internal surfaces that at least partially define a respective one of the voids of the first and second housings, the first pair of opposed internal surfaces spaced along the second direction and the second pair of opposed internal surfaces spaced along the third direction.

4. The expandable spacer implant of claim 1, wherein the distracting member is disposed between the internal surfaces of the first and second pairs of internal surfaces.

5. The expandable spacer implant of claim 1, wherein the second housing defines a proximal side and a groove that extends from the proximal side and through one of the internal surfaces of the first pair of opposed internal surfaces so as to provide access to an instrument engagement feature defined by the distracting member.

6. The expandable spacer implant of claim 1, wherein the inner surface of the first housing defines a first recess, the inner surface of the second housing defines a second recess, and the distracting member defines opposed protrusions that are configured to engage the first and second recesses.

7. The expandable spacer implant of claim 1, further comprising a stabilizer that protrudes beyond the outer surface of at least one of the first and second housings when the first and second housings are fully distracted apart.

8. The expandable spacer implant of claim 1, wherein the second pair of internal surfaces extend from the middle portion of the implant towards both the proximal-most side of the implant and the distal-most side of the implant.

9. The expandable spacer implant of claim 1, wherein the void extends into inner surface of the second housing midway between the proximal-most side of the implant and the distal-most side of the implant.

10. The expandable spacer implant of claim 1, wherein each of the first and second housings has a continuous one-piece body that extends from the proximal-most side of the implant to the distal-most side of the implant.

11. The expandable spacer implant of claim 1, wherein the expandable spacer implant is an expandable interspinous spacer implant configured to be inserted into an interspinous space that is defined between a spinous process of the superior vertebral body and a spinous process of the inferior vertebral body.

12. An expandable spacer implant configured to be inserted into a space that is defined between a superior vertebral body and an inferior vertebral body, the implant comprising:
   a first housing having an outer surface configured to engage one of the superior and inferior vertebral bodies, an inner surface spaced from the outer surface along a first direction, and first and second sides that are spaced from one another along a second direction, perpendicular to the first direction;
   a second housing having an outer surface configured to engage another of the superior and inferior vertebral bodies, the second housing further having an inner surface that faces the inner surface of the first housing and is spaced from the outer surface of the second housing along the first direction, and first and second sides that are spaced from one another along the second direction, the first and second sides of the second housing having first and second slots, respectively, formed therein, each slot being defined between a pair of internal surfaces of the second housing that are spaced along the first direction;
   a first wing member rotatably coupled to the first side of the first housing and translatably coupled to the first slot of the second housing such that the first wing member translates along a third direction, perpendicular to both the first and second directions; and
   a second wing member rotatably coupled to the second side of the first housing and translatably coupled to the second slot of the second housing such that the second wing member translates along the third direction,
   wherein the expandable spacer implant is configured to expand from a collapsed configuration to an expanded configuration such that the first and second housings move away from one another in the first direction while the first and second wings each remain coupled to both the first and second housings.

13. The expandable spacer implant of claim 12, wherein:
   the first and second sides of the first housing having third and fourth slots, respectively, formed therein, each slot being defined between a pair of internal surfaces of the first housing that are spaced along the first direction; and
   the implant further comprises a third wing member rotatably coupled to the first side of the second housing and translatably coupled to the third slot of the first housing, and a fourth wing member rotatably coupled to the second side of the second housing and translatably coupled to the fourth slot of the first housing.

14. The expandable spacer implant of claim 13, wherein the first, second, third, and fourth wing members have extensions that are deployed as the first and second housings are distracted apart from each other.

15. The expandable spacer implant of claim 12, wherein each of the first and second slots is at least partially defined by a closed shape defined on the first and second sides, respectively, of the second housing.

16. The expandable spacer implant of claim 12, wherein each pair of internal surfaces is between the inner and outer surfaces of the second housing with respect to the first direction.

17. The expandable spacer implant of claim 12, wherein each of the first and second wing members has an extension that protrudes beyond the outer surface of the second housing when the implant is in an expanded position in a direction that extends from the inner surface of the second housing toward the outer surface of the second housing.

18. The expandable spacer implant of claim 12, further comprising a first cover that covers the first side of the first housing, a second cover that covers the second side of the first housing, a third cover that covers the first side of the second housing, and a fourth cover that covers the second side of the second housing.

19. The expandable spacer implant of claim 12, further comprising a first securement pin that rotatably couples the first wing member to the first side of the first housing, a first guidance pin that translatably couples the first wing member to the first slot, a second securement pin that rotatably couples the second wing member to the second side of the first housing, and a second guidance pin that translatably couples the second wing member to the second slot.

* * * * *